(12) United States Patent
Doke

(10) Patent No.: US 11,710,548 B1
(45) Date of Patent: Jul. 25, 2023

(54) VIRTUAL QUALITY CONTROL SYSTEM AND METHOD

(71) Applicant: Cornerstone Automation Systems, LLC, Frisco, TX (US)

(72) Inventor: Michael J. Doke, Frisco, TX (US)

(73) Assignee: Cornerstone Automation Systems, LLC, Frisco, TX (US)

( * ) Notice: Subject to any disclaimer, the term of this patent is extended or adjusted under 35 U.S.C. 154(b) by 339 days.

(21) Appl. No.: 15/221,881

(22) Filed: Jul. 28, 2016

Related U.S. Application Data

(60) Provisional application No. 62/197,930, filed on Jul. 28, 2015.

(51) Int. Cl.
| | |
|---|---|
| *G16H 20/13* | (2018.01) |
| *G06Q 30/06* | (2023.01) |
| *G06Q 30/00* | (2023.01) |
| *G06Q 30/0601* | (2023.01) |
| *G06Q 30/018* | (2023.01) |
| *G06V 20/00* | (2022.01) |

(52) U.S. Cl.
CPC .............. *G16H 20/13* (2018.01); *G06Q 30/018* (2013.01); *G06Q 30/0637* (2013.01); *G06V 20/00* (2022.01)

(58) Field of Classification Search
CPC ... B65B 57/00; G06Q 30/018; G06Q 30/0637; G16H 20/13; G06F 19/3462
See application file for complete search history.

(56) References Cited

U.S. PATENT DOCUMENTS

| | | | | | |
|---|---|---|---|---|---|
| 4,524,869 | A | * | 6/1985 | Nader | B65D 83/0463 206/533 |
| 2011/0184751 | A1 | * | 7/2011 | Holmes | G06F 19/3462 705/2 |
| 2013/0197693 | A1 | * | 8/2013 | Kamen et al. | G06F 21/32 700/244 |

FOREIGN PATENT DOCUMENTS

EP          1416451 A2 *   5/2004 ................. G07F 11/62

OTHER PUBLICATIONS

Follow The Pill: Understanding the U.S. Commercial Pharmaceutical Supply Chain, The Health Strategies Consultancy LLC (Year: 2005).*

* cited by examiner

*Primary Examiner* — Aryan E Weisenfeld

(57) ABSTRACT

A virtual quality control system and a method for virtual quality control of an automated medication fulfillment process are disclosed herein. In one aspect, the disclosure provides a virtual quality control system. In one embodiment, the virtual quality control system includes: (1) a verification controller configured to receive visual verification data and identification data of a verification event and generate comparison data from the identification data, and (2) a verification station configured to send a verification status to the verification controller based on the comparison data, the visual verification data, and input from a verifier.

13 Claims, 6 Drawing Sheets

VIRTUAL QUALITY CONTROL SYSTEM AND METHOD

CROSS REFERENCE TO RELATED APPLICATION

This Application claims the benefit of U.S. Provisional Application Serial No. 62/197,930 filed on Jul. 28, 2015, entitled "VIRTUAL QUALITY CONTROL SYSTEM," by Michael J. Doke, commonly assigned with the present invention and incorporated herein by reference in its entirety.

TECHNICAL FIELD

This application is directed to quality control in automated order fulfillments and, more specifically, to visual verification of an action or an event in automated fulfillment systems.

BACKGROUND

The need for automated fulfillment systems has increased as companies develop centralized locations to fulfill and ship orders for a variety of goods. The increase of on-line retail orders has also fueled the development of automated fulfillment systems since multiple consumers can order products to be shipped to them while in the comfort of their own homes. This is even true for prescription drugs where the availability of internet access has allowed consumers to purchase prescription drugs on-line.

The number of people on prescription drugs has increased and, as population's median age continues to increase, the number of those on prescription drugs will mostly likely continue to increase as well. Additionally, large health care providers, such as the Veteran's Administration and similar governmental administered health care programs, have seen increased prescription needs of the patients that they serve. In view of this growing fulfillment need, large prescription service providers have arisen. With the advent of these large prescription suppliers, shipment or order fulfillment has grown significantly within the last few years to meet the public's growing prescription needs.

SUMMARY

In one aspect, the disclosure provides a virtual quality control system. In one embodiment, the virtual quality control system includes: (1) a verification controller configured to receive visual verification data and identification data of a verification event and generate comparison data from the identification data, and (2) a verification station configured to send a verification status to the verification controller based on the comparison data, the visual verification data, and input from a verifier.

In another aspect, a method for virtual quality control of an automated medication fulfillment process is disclosed. In one embodiment, the method includes: (1) virtually verifying a type of medication placed in a canister, (2) virtually verifying a label associated with a medicine container, and (3) virtually verifying an amount of the medication placed in the medicine container from the canister.

In yet another aspect, another virtual quality control system is disclosed. In one embodiment, the virtual quality control system includes: (1) a camera configured to obtain visual verification data at an input location of a verification event, (2) an event monitor configured to obtain identification data at the input location, (3) a verification controller configured to receive the visual verification data and the identification data, and generate comparison data from the identification data, and (4) a verification station configured to receive the visual verification data and the comparison data from the verification controller, and determine a verification status based on the comparison data, the visual verification data, and an input from a verifier.

BRIEF DESCRIPTION

Reference is now made to the following descriptions taken in conjunction with the accompanying drawings, in which.

DETAILED DESCRIPTION

Figure 1:
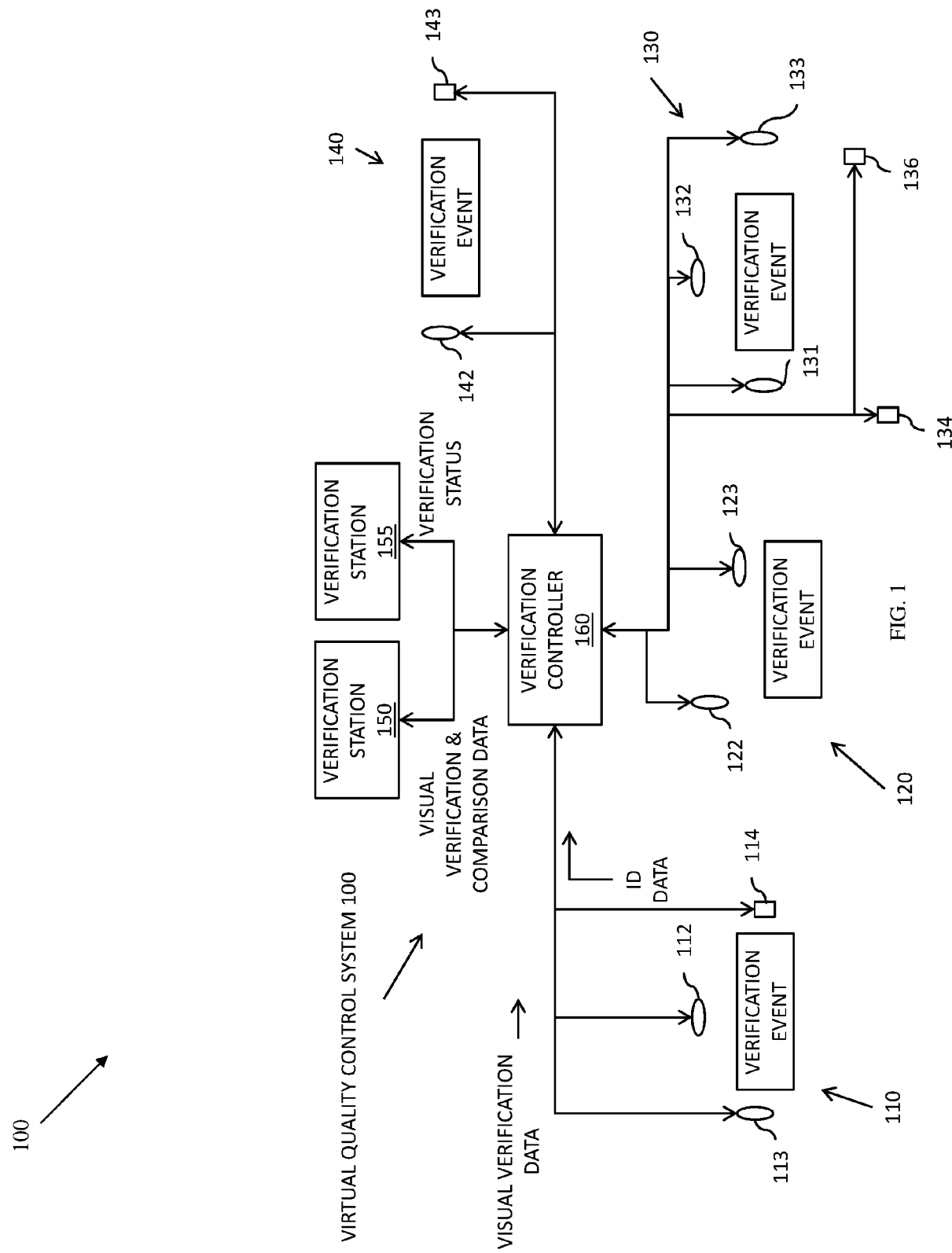
FIG. 1 illustrates a block diagram of an embodiment of a virtual quality control system constructed according to the principles of the disclosure.

Unlike traditional retail products, fulfilling prescription orders can be difficult to automate due to the safeguards that are needed when fulfilling these orders. Though automated fulfillment systems can include various checks to make sure that orders are correctly filled, filling prescriptions provide a different challenge. For example, to insure prescriptions are correctly filled, some states still require verification of prescriptions from a pharmacist even in mass fulfillment systems. Manual verification of the prescriptions, however, can slow down the fulfillment process and greatly reduce the benefit of automated order fulfillments.

Accordingly, the disclosure provides a virtual quality control system that allows a person or persons (i.e., a verifier) to visually verify that an order has been correctly filled by an automated fulfillment system based on visual images. The visual images (i.e., images) allow the verifier to be absent from the actual location where the order is filled. As such, the verifier can be remotely located from the automated fulfillment system. In some embodiments, the verifier can be proximate the location of the automated fulfillment system, such as in the same room, in another room of the same building or in a proximate building. In other embodiments, the verifier can be distal from the location of the automated fulfillment system, such as in another city, county or state.

The verifier can be a skilled verifier who is licensed in a certain occupation and is recognized to manually perform the action that is automatically being done and needing verification. The skilled verifier can be licensed by a government entity, e.g., a federal or state entity. In some embodiments the licensing agency is the entity that is requiring visual verification that a verification event was performed properly. For example, a skilled verifier can be a pharmacist for verifying the correct filling of prescriptions in an automated medication fulfillment system. Accordingly, in one embodiment the disclosed virtual quality control system advantageously incorporates required visual verification from a pharmacist with the automated fulfillment systems to satisfy verification laws and maintain the automated fulfilling of prescriptions.

An automated fulfillment system includes one or more fulfillment stations that use animatronics, such as robotic arms, to attach coded labels onto containers, fill the containers with the appropriate product and organize grouped orders within the system. The automated fulfillment system can include a conveyor belt or belts that move the products to the multiple fulfillment stations. The automated fulfillment systems can be fully or highly automated fulfillment systems (e.g., robotic systems). In one embodiment, the automated fulfillment system is an automated medication fulfillment system that includes one or more fulfillment stations that use animatronics to attach coded labels onto medication containers (e.g., bottles, blister packs, box, unit of use items), fill the containers with the appropriate medication if needed (i.e., not a unit of use item) and organize grouped medication orders within the system.

The overall automated fulfillment systems disclosed herein are controlled by one or more controllers that have a sufficient number of microprocessors, memory, communication circuitry, and software algorithms associated therewith to provide instructional commands to the various fulfillment apparatuses. The one or more controllers may communicate, wirelessly or by hard wire, with one or more sub-controllers located at each given fulfillment station, or it may communicate with sub-controllers associated with individual pieces of equipment that are used in the automated fulfillment system. Alternatively, a number of individual controllers may cooperatively communicate, wirelessly or by hard wire, with each other to direct the various functions of the fulfillment system.

A verification event as used herein is an action or part of an automated fulfillment process or an automated fulfillment system that is to be visually verified by a person that it was correctly performed. In some embodiments, the visual verification of the verification event is required. Verification of a particular event or action could be required by a law, e.g., state or federal. For example, a pharmacist may be required to visually verify that prescriptions are correctly filled. In some embodiments, the requirement can be due to industry standards or company policy. A verification event may not be the actual event that requires visual verification but is an action or event that contributes to the overall automated process that does need visual verification. For example, the actual filling of a prescription bottle may require visual verification and a verification event is the filling of a canister that includes medication that later is used by the automated medication fulfillment system to fill the prescription bottle with the correct medication.

The verification event can be part of a unique, unconventional automated fulfillment system that a supplier may use to fulfill orders, such as an automated medication fulfillment system used to fulfill prescriptions. An automated medication (e.g., capsules or tablets) fulfillment process can accommodate various shapes and sizes of pills, both prescription drugs and over-the-counter medications or vitamins manufactured in tablet or capsule form (hereinafter referred generically to as "medication" or "medications"). A medication includes a narcotic drug or other controlled substance. A target medication, as used herein, is one that is intended to be filled by a fulfillment supplier for a particular order or prescription.

FIG. 1 illustrates a block diagram of an embodiment of a virtual quality control system 100 constructed according to the principles of the disclosure. The various features and design of the virtual quality control system 100 can be advantageously employed with an automated fulfillment system as described above, including an automated medication fulfillment system. The virtual quality control system 100 includes input locations 110, 120, 130, 140, verification stations 150, 155, and a verification controller 160. One skilled in the art will understand that the virtual quality control system 100 can include more input locations and verification stations or even fewer input locations and verification stations as illustrated. Additionally, one skilled in the art will understand that there can be more than one verification controller 160. The various components of the virtual quality control system 100 can be communicatively coupled via conventional wired or wireless connections.

The input locations 110-140 are locations of an automated fulfillment system where verification events occur and visual verification data of the verification event is generated. Visual verification data is a visual image or visual images of the verification event. The visual verification data can be video images or still images. As illustrated in FIG. 1, there can be multiple input locations. The visual verification data at each input location 110-140 is generated by a camera or cameras. In some embodiments, at least two cameras are used to generate the visual verification data. The cameras at each of the input locations 110-140 can be the same type or can be different types of cameras. The position or location of the cameras can be static or dynamic. In one embodiment, the cameras are video cameras. In some embodiments the cameras are high speed, still cameras. In various embodiments, the cameras can be remotely controlled. A verifier can use a user interface at the verification station 150 or 155, to control the different cameras. In some embodiments, a verifier can use the user interface to zoom in on the visual verification data that is already received at the verification station 150 or 155. As such, a verifier can zoom in or zoom out when reviewing a verification event. The type of cameras and the positioning of the cameras at the input locations 110-140 can be based on the type of verification event.

Figure 5:
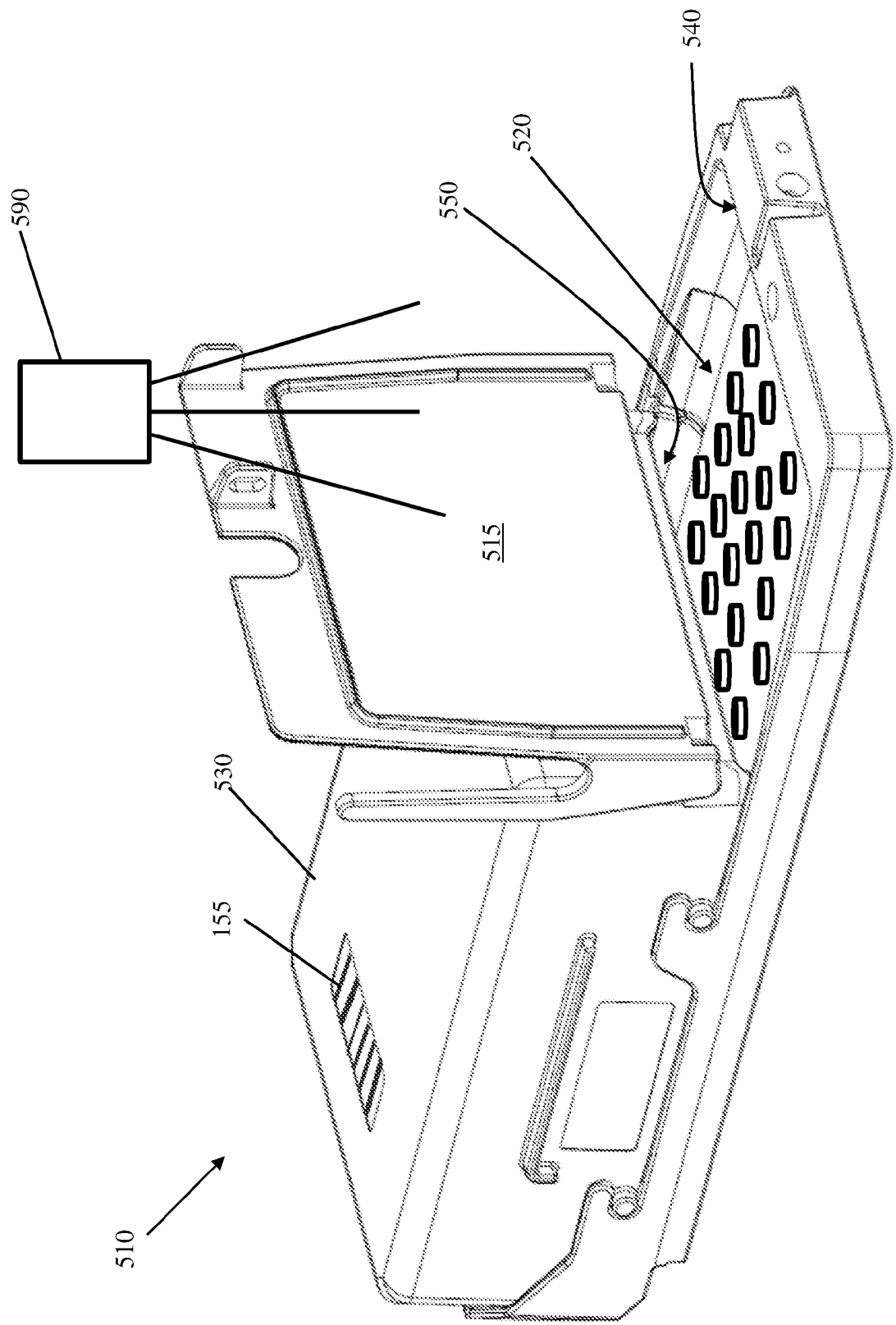
FIG. 5 illustrates a diagram of a portion of an embodiment of another input location constructed according to the principles of the disclosure.

Consider for example input location 110, the verification event can be filling a bottle with medication by an automated medication fulfillment system according to a prescription being filled. As such, camera 112 can be positioned above the bottle on the automated fulfilment system to generate visual verification data that the bottle has been filled with the correct medication. Additional visual verification data can be provided by camera 113 that is positioned to show the medication going into the bottle. Either camera 112, camera 113 or both cameras 112, 113, can also be used to indicate the amount or number of medication that is being put in the bottle. FIG. 5 and the corresponding discussion provide further information on an input location that determines the number of medication to put in a bottle.

The input location 110 also includes an event monitor 114 that is configured to obtain identification (ID) data for the verification event at input location 110. The ID data identifies a part or product of the verification event. The verification controller 160 employs the ID data to provide comparison data to the verification station 150. The verification station 150 employs the comparison data to verify the verification event was performed correctly. For example, the ID data can indicate the type of medication that is to be loaded into a bottle for an automated medication fulfillment system.

In addition to being used for the virtual quality control system 100, the ID data is also used by the automated fulfillment system associated therewith. For example, conveyor belts of the automated fulfillment system may have a scanner or camera associated therewith that scans the above-discussed ID data to identify the containers and its contents. The controller(s) of the automated fulfillment system can then use the scanned data to coordinate other fulfillment processing steps of the automated fulfillment system.

The event monitor 114 can be an optical scanner or RF receiver that obtains the ID data from a bar code area on a container, such as a bottle, or an electronic identification chip or tag, such as a radio frequency identification (RFID) tag, located thereon. When a bar code is used, it may be any known type of bar code, for example, it may be a straight-line bar code or it may be a design code, such as an Aztec Code, a CrontoSign code, a Data Matrix code or a SPARQ-Code, to name just a few. In those embodiments that use an RFID tag or other known electronic identification technology, the electronic identification tag or chip may attach to the surface of the bottle or be embedded within the bottle.

Continuing with the above example of filling a bottle with medication, the ID data indicates a particular medication. A memory of, associated with or accessible by the verification controller 160 relates the ID data to the particular medication via, for example, a data table. The verification controller 160 then uses this ID data to obtain comparison data for verification and provides the comparison data and the visual verification data to the verification station 150 or 155. The comparison data can be a picture of the particular medication. The comparison data can also include dimensions that correspond to the medication.

The event monitor 114, therefore, can be used to read the ID data which is then used to confirm the type of medication by cross-referencing the stored data in a database. A system controller for the automated fulfillment system can perform this cross-referencing to confirm the medication. Additionally, the ID data can be used by the verification controller 160 to obtain the comparison data by cross-referencing stored data in a database associated with the verification controller 160.

As illustrated, the input locations 110-140 can have a different number of cameras and event monitors. In some embodiments, an input location does not even have an event monitor. If ID data is needed, then a camera can be used to determine the ID data by conventional means. For example, input location 120 has cameras 122, 123, and no event monitor. Input location 130 includes multiple cameras 131, 132, 133, and multiple event monitors 134, 136. In contrast, input location 140 includes a single camera 142 and a single event monitor 143. The various camera and event monitor configurations at the different input locations illustrated in FIG. 1 provide some examples of the configurations that can be used.

The verification controller 160 receives visual verification data and the ID data from the input locations 110-140. The different cameras and event monitors at the input locations 110-140 can be communicatively coupled to the verification controller 160 via conventional wireless or hardwired connections. The verification controller 160 provides the visual verification data and comparison data to at least one of the verification stations 150, 155, for reviewing.

Each of the verification stations 150, 155, is where a skilled verifier reviews the visual verification data and determines if the verification event was performed properly. The verification stations 150, 155, include a computing device having a screen and a user input device. The screen displays the visual verification data from the input station 110 and the comparison data. A verifier approves or disapproves the verification event based on a comparison between the visual verification data and the comparison data. The verifier employs the user input device to indicate the verification status, i.e., approved or disapproved. As noted above, the verifier can be a skilled verifier.

In some embodiments, the visual verification data includes multiple images from different cameras that the skilled verifier employs to approve or disapprove. For example, one image of the visual verification data can include a label of a prescription bottle and another image can be the medication in the prescription bottle. Both of these images can be displayed on the screen at the same time and a skilled verifier can compare the two to insure that the correct medication is in the bottle. More details of an embodiment of a verification station are provided with respect to FIG. 2.

The verification controller 160 is configured to direct the operation of the virtual quality control system 100. The verification controller 160 may be an integrated controller or a distributed controller that directs operation of the virtual quality control system 100. The verification controller 160 may include an interface to receive visual verification data and the ID data. The verification controller 160 also includes a processor, such as a microprocessor, to direct the operation of the virtual quality control system 100. The processor can be configured to direct operation of the virtual quality control system 100 according to industry standards, laws, per the directions of a client, etc.

The verification controller 160 may include a memory section having a series of operating instructions stored therein that direct the operation of the verification controller 160 (e.g., the processor) when initiated thereby. The series of operating instructions may represent algorithms that are used to control the virtual quality control system 100. The memory or another memory of the verification controller 160 is also configured to store the comparison data and ID data.

The verification controller 160 receives the visual verification data and the ID data from the various input locations 110-140 and provides the verification stations 150, 155, with the visual verification data and comparison data for verification. The verification controller 160 can be a single computing device or can be multiple computing devices that cooperate to direct the operation of the virtual quality control system 100. As such, the functionality of the verification controller 160 can be distributed.

In one embodiment, the verification controller 160 is configured to respond to the received verification status or statuses with a response action. For an approved verification status, the response action can maintain the system as presently working. For an unapproved verification status, the response action can be a corrective action. In one embodiment the corrective actions include increasing the sample rate for the verification event, increasing the sample rate for a related verification event, removing unapproved filled containers from the line and buffering the filled containers for additional verification (either virtual from another verifier or a person on site). One skilled in the art will understand that other corrective actions to insure the quality of the fulfillment system besides those listed here can also be performed. In some embodiments, more than one corrective action may be employed in response to an unapproved verification status.

In some embodiments, the verification controller 160 is configured to provide the verification status to the controller for the automated fulfillment system to respond with a response action. The automated fulfillment system controller (not shown) is configured to control the automated fulfillment system according to the determined response action. The verification controller 160 and controllers or controller of the automated fulfillment system can cooperate to perform the determined response action.

The verification controller 160 is configured to control the sample rate for verifying events. The sample rate can vary for different events and can vary over time. The sample rate can be determined for a particular line or input location 110-140. The sample rate can be determined by a customer or by a governing body and can correspond to a desired quality control level. The sample rate can be one hundred percent for the actual filling of a prescription bottle whereas the sample rate for checking filled prescription bottles is one percent. Accordingly, for every one hundred filled prescription bottle, a virtual verification is performed. In some embodiments, multiple approved verification statuses can prompt a response action that lowers the sample rate. Additionally, disapproved verification statuses can result in a response action that increases the sample rate. Thus, the sample rate can be dynamic and can be controlled by the verification controller 160.

The verification controller 160 is also configured to administer a training program for verifiers and a quality control program for the verifiers. In one embodiment, the training program uses predetermined visual data and comparison data for training. In other embodiments, the training program can use real-time data from an operating automated fulfillment system but the verification status does not affect the operation of the line. The training program can allow a verifier to control the rate of review for practice using a user interface.

The verification controller 160 is also configured to administer a quality control program to monitor the work of verifiers. The quality control program can monitor the time it takes a verifier to review to insure the review time corresponds to a desired range. In one embodiment, the review time range can be between four to six seconds. If the review time is below the minimum, then the verifier may not be adequately checking. If the review time is above the maximum, then the verifier is taking too long. Accordingly, the verifier may need to spend more time with the training program. The verification controller 160 can also send known problems or failures as part of the quality control program to check the accuracy of the verifiers and to keep them alert.

The verification controller 160 is also configured to optimize the verification process. The verification controller 160 can optimize the verification process by determining which verifier is better suited for a particular verification, mixing the input locations for each verification station, changing the presentation of the visual verification data and the comparison data on the screen of the verification stations 150, 155, randomly interrupting the verification process with a quiz, contest for prizes, pictures, or other strategies to keep verifiers alert.

In some embodiments, a visual verification system may include a single verification controller. In other embodiments, a visual verification system may include multiple verification controllers. In such embodiments, each one of the multiple verification controllers can be connected to mutually exclusive input locations 110-140. As such, each verification controller can be assigned to specific input locations 110-140 or even a single one of the input locations.

Additionally, each one of the multiple verification controllers can be communicatively coupled to mutually exclusive verification stations or some of the multiple verification controllers can be communicatively coupled to some or even all of the same verification stations. If there are multiple verification controllers, they are communicatively coupled together.

Figure 2:
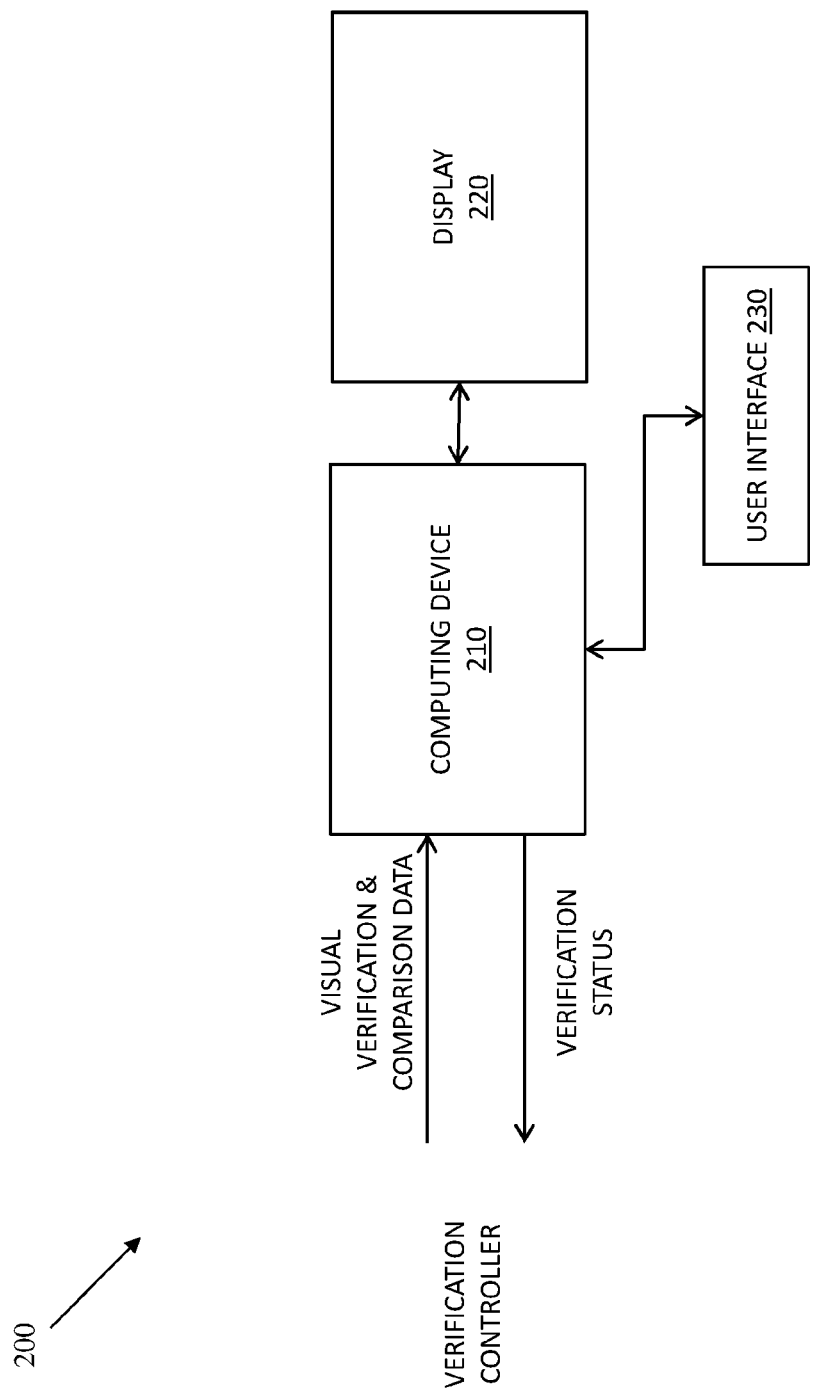
FIG. 2 illustrates a block diagram of an embodiment of a verification station constructed according to the principles of the disclosure.

FIG. 2 illustrates a block diagram of an embodiment of a verification station 200 constructed according to the principles of the disclosure. The verification station 200 includes a computing device 210, a display 220 and a user input device 230. Each of the components can be connected via hard wired or wireless connections. In some embodiments, the display 220 is integrated with the computing device 210. Additionally, in some embodiments the user interface 230 can be integrated with the display 220. For example, the display 220 can include a touchscreen.

The computing device 210 is configured to direct the operation of the verification station 200. The computing device includes a processor for controlling the operation. Additionally, the computing device 270 may include an interface and a memory coupled thereto. The interface can be a conventional interface having multiple ports for transmitting and receiving data, such as data from a verification controller. The memory section can be a conventional memory that is constructed to store data and computer programs.

The display 220 is configured to display an image or images on a screen for viewing. As noted above, the screen can be a touchscreen. Accordingly, the display 220 can visually provide information to a verifier and receive inputs from the verifier. The verification controller 160 can control the information provided to the display 220 and the presentation of the information on the screen of the display. The information can be the visual verification data and the comparison data.

The user interface 230 is configured to provide inputs from a verifier to the computing device 210. Both the display 220 and the user interface 230 can be conventional devices. The user interface 230, for example, can be a mouse, a pointing device, a keyboard, a keypad, a speaker, a footpad, etc. In some embodiments, the user interface 230 is a specially designed device for receiving inputs from a verifier to indicate an approved or disapproved verification status. For example, the user interface 230 can be an input device that has components specifically designed to receive an approved or disapproved input from a verifier. The user interface 230 can be used to zoom in on the visual verification data.

The computing device 210 receives inputs from the verification controller 160, such as the visual verification data and comparison data, and provides the inputs on the display 220 for viewing. The display 220 displays the visual verification data and the comparison data from an input station for reviewing. A verifier visually reviews and approves or disapproves the verification event based on a comparison between the visual verification data and the comparison data. The verifier employs the user input device 230 to indicate the verification status.

In some embodiments, dual inputs from a verifier are needed to indicate the verification status. For example, a verifier may need to verbally affirm approval and also indicate approval via another user interface, such as keyboard, mouse, or keypad. In some embodiments, the dual inputs need to be simultaneous to register approval or disapproval. The verification controller 160 can determine when dual inputs are needed or required. The verification controller 160 can randomly require dual inputs to keep verifiers engaged.

In some embodiments, the visual verification data includes multiple images from different cameras that the verifier employs to approve or disapprove. For example, one image of the visual verification data can include a label of a prescription bottle and another image can be the medication in the prescription bottle. Both of these images can be provided by the display 220 at the same time and the skilled verifier can compare the two to insure that the correct medication is in the bottle. Comparison data can also be displayed to assist in verification.

Figure 3:
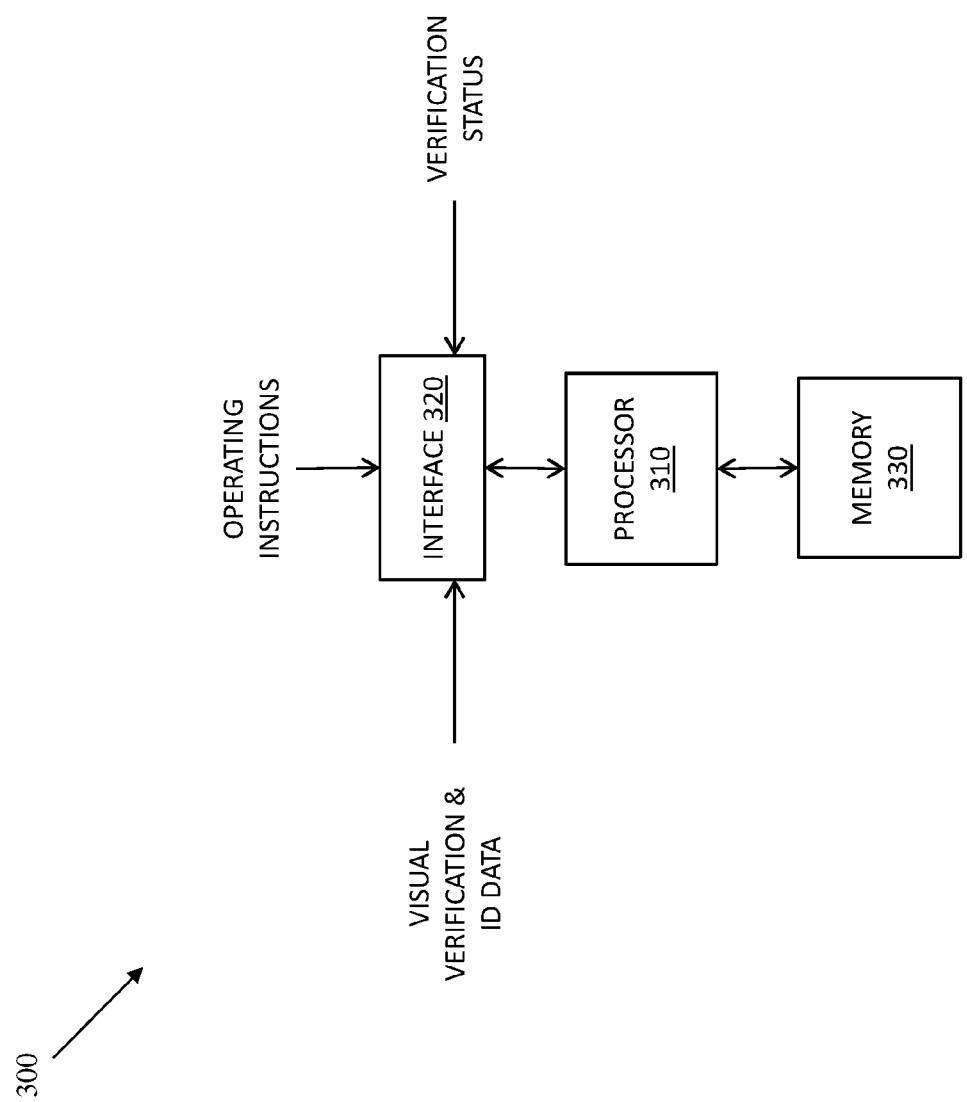
FIG. 3 illustrates a block diagram of an embodiment of a verification controller constructed according to the principles of the disclosure.

FIG. 3 illustrates a block diagram of an embodiment of a verification controller 300 constructed according to the principles of the disclosure. The verification controller 300 includes a processor 310 that is configured to direct the operation of the verification controller 300 to control a virtual quality control system. The processor 310 may be a conventional processor such as a microprocessor. Additionally, the verification controller 300 includes an interface 320 and a memory 330 coupled thereto. One skilled in the art will understand that the verification controller 330 can include additional components typically included with a controller such as a power supply or power port.

The interface 320 includes multiple ports for transmitting and receiving data from at least the cameras and event monitors positioned at input locations. The interface 320 can support wireless or wired communications. Additionally, the interface 320 can receive programming to direct the operation of the virtual quality control system. The programming instructions can be encrypted for security. The programming instructions can correspond to the desires or operation protocols of different clients. As such, the verification controller 300 can be configured to control the same type of virtual quality control system differently according to the client. In some embodiments, the programming instructions can be received from a remote location.

The memory section 330 may be a conventional memory located within a controller that is constructed to store data and computer programs. The memory 330 may store operating instructions such as control signals to direct the operation of the processor 320 when initiated thereby. The operating instructions may correspond to algorithms that provide the functionality of the operating schemes disclosed herein. The memory section 330, therefore, stores the programming instructions that direct the operation of the virtual quality control system.

Figure 4:
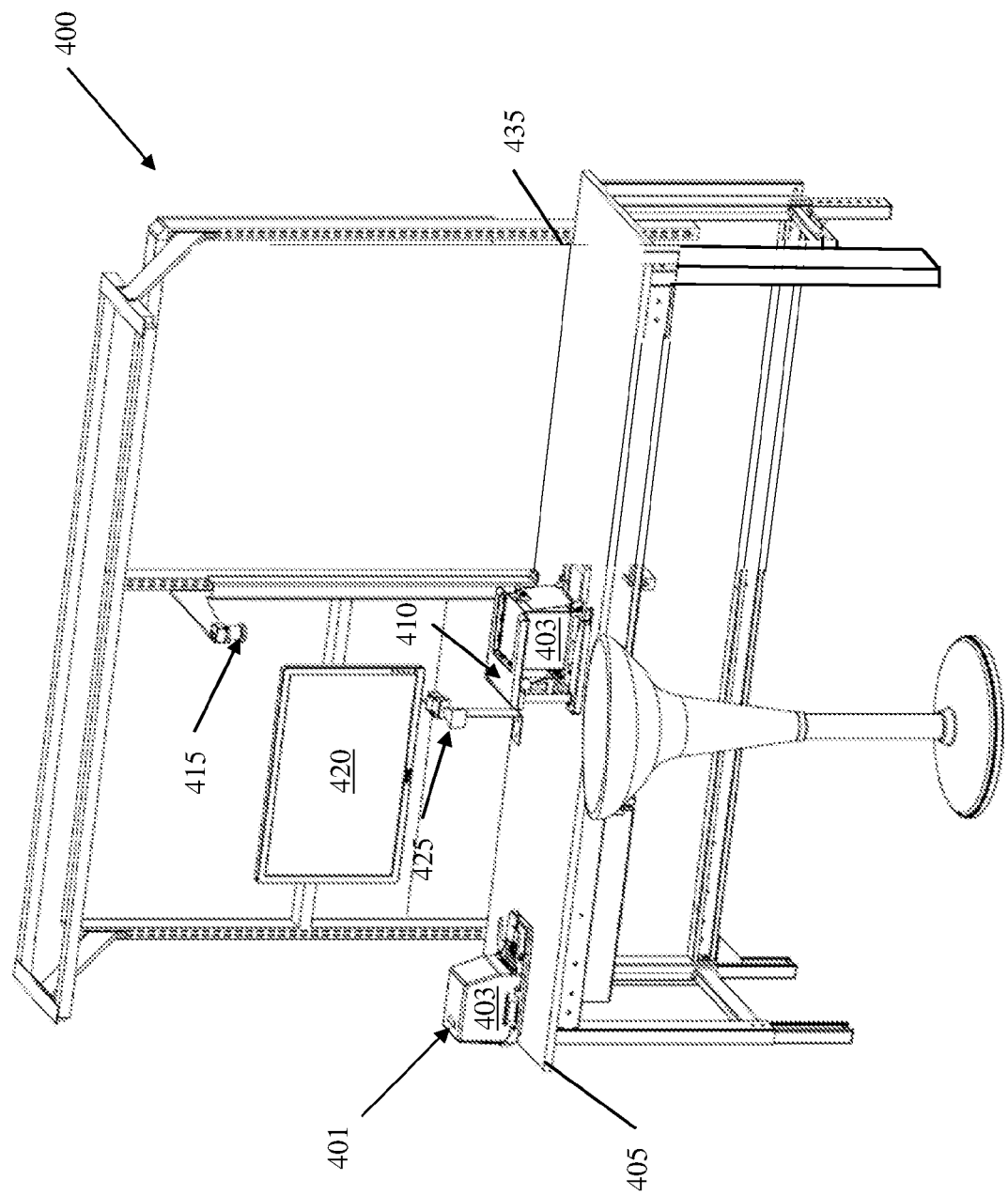
FIG. 4 illustrates a diagram of a medication supplying station that is used to supply a canister with a target medication and is an example of an input station according to the principles of the disclosure.

FIG. 4 and FIG. 5 illustrate examples of input stations that correspond to fulfillment stations of an automated medication fulfillment system. FIG. 4 illustrates a diagram of an embodiment of an input location 400 constructed according to the principles of the disclosure. The input location 400 is a filling station that is used to supply a canister 100 with a target medication. The input location 400 is an example of a verification event that is performed manually and is verified via a virtual quality control system. One skilled in the art will also understand that an animatronic device could also perform the verification event and still be visually verified via a virtual quality control system.

At the input location 400, empty canisters 401 are placed on a workbench 405, after which the canister 401 is disassembled using a disassembly rack 410, which is designed to hold a dispensing compartment 403 in place while a bottom thereof is removed. The removal of the bottom exposes the interior of the dispensing compartment 403, which allows the placement of the correct type and number of the target medication in the dispensing compartment 403. A manual operator supplies the dispensing compartment 403 with the correct type and amount of target medication from a main supply source (not shown).

Additionally, an event monitor 425, such as an optical scanner, scans the target medication supply ID data and inputs it into a database for crosscheck and reference to the correct canister 401, during the fulfillment process. The automated medication fulfillment system's controller(s) identifies the supply source medication that has ID data that matches the canister's 401 ID data and associates that identified medication with the canister 401 using their respective ID data. Additionally, the ID data is applied to the canister 401 so that the automated medication fulfillment system controller(s) can use other scanners to determine that the canister 401, and therefore the target medication, is correct for a given fulfillment station. A screen 420 may also display the data relating to the amount and type of medication placed into the container.

As the dispensing compartment 403 is supplied with the target medication, a camera 415 is positioned to provide visual verification data of the filling process for remote viewing of the filling process by a pharmacist at a verification station that can confirm that the amount and type of the target medication are correct. When the pharmacist approves the dispensing compartment 403 is supplied with the proper amount and type of medication, a manual operator places the bottom back onto the dispensing compartment 403, using the disassembly rack and locks the tray lid in the closed position. The supplied canister 401 can then be placed onto a holding rack 435 for distribution to the appropriate fulfillment station of the automated medication fulfillment system.

FIG. 5 illustrates a diagram of a portion of an embodiment of an input location 500 constructed according to the principles of the disclosure. The input location 500 is a medication dispensing station where the medication is dispensed to be placed in a bottle using the automated medication fulfillment system. A supplied canister 510 and a camera 590 are illustrated. At the dispensing station, the fulfillment system's controller signals a vibrator unit to vibrate for a prescribed time. During the vibration cycle, target medication 520 flows from the dispensing compartment 530 to the tray portion 540 through an opening 550. FIG. 5 provides an example of using the virtual verification system for visual verification an automated process.

The supplied canister 510 is shown with the medication 520 dispensed in the tray portion 530 of the canister 510 when in a full open position. When a tray lid 515 of the canister 510 is unlocked via an automated means, a robotic arm (not shown) opens the tray lid 515 to a fully open position as illustrated in FIG. 5. In one embodiment, the tray portion 540 allows light to come through from its underside, effectively backlighting the medication 520. This enhances the medication's 520 image and aides in the identification of the medication 520 by the camera 590. The camera 590 provides verification data for the virtual quality control system for review by a pharmacist that the medication 520 is of the correct type and shape and not broken or damaged in any way. The verification data is sent to a verification station.

Figure 6:
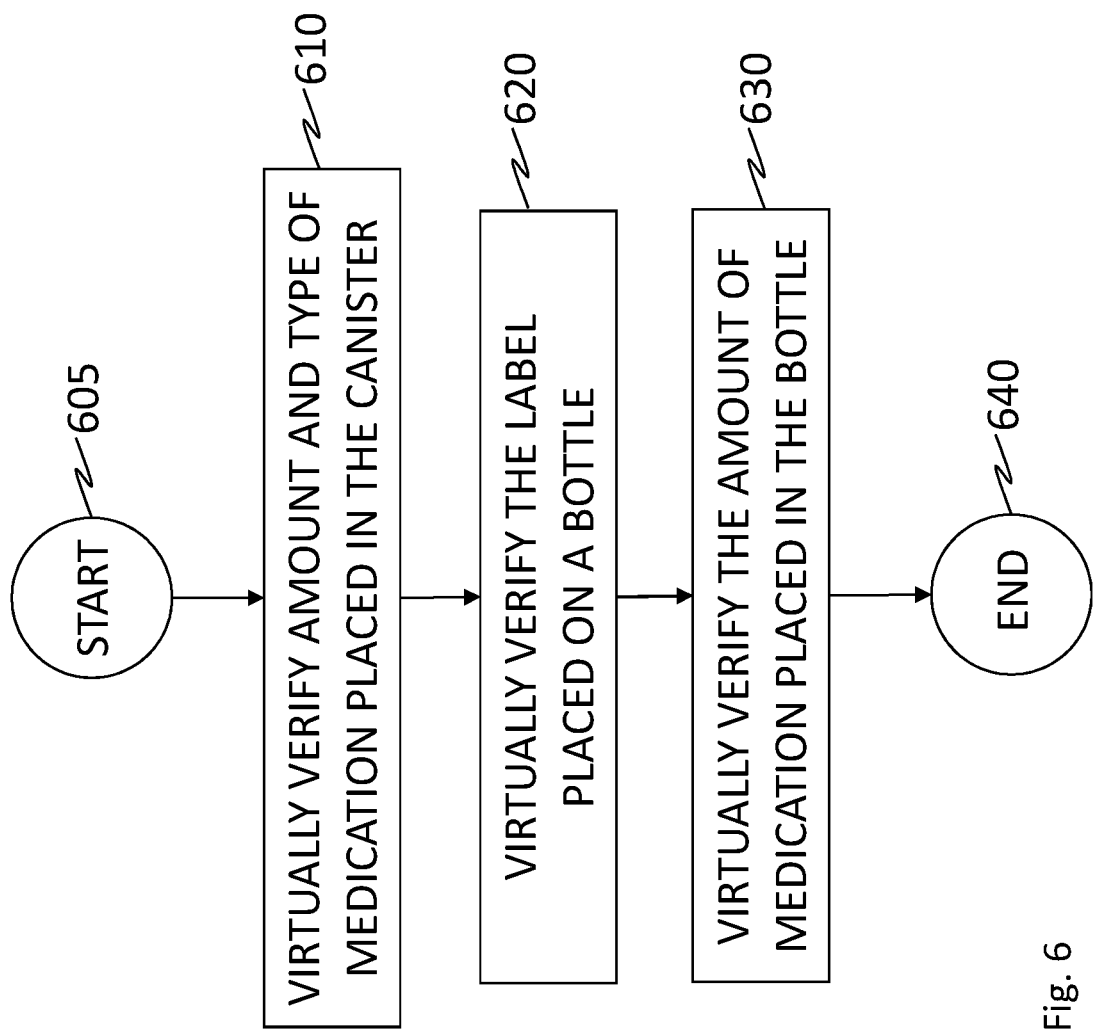
FIG. 6 illustrates a flow diagram of an embodiment of a method of a virtual quality control process carried out according to the principles of the disclosure.

FIG. 6 provides a flow diagram of one embodiment of a method of a virtual quality control process 600 carried out according to the principles of the disclosure. The process 600 is described with respect to an automated medication fulfillment process. One skilled in the art will understand that there may be additional virtual visual verification steps associated with the automated medication fulfillment system. For example, an additional visual verification step can be verifying that a prescription bottle was filled correctly by the automated medication fulfillment system. When a supplier receives an order for a target medication, the type of medication, patient or customer's name, and other salient identifying data are entered into the memory of the fulfillment system. Typically, a supplier may receive multiple orders of the same type of medication for different patients. Thus, an automated medication fulfillment process as presented herein is particularly advantageous in such situations. A manual operator or automated system places the target medication into the canister's dispensing compartment. The virtual quality control process 600 begins in a step 605. Each step of the process 600 can be performed by a virtual quality control system as described herein.

The type and amount of medication placed in the canister is virtually verified in a step 610. The canister receives an identification code, as discussed above, that matches the type and amount of the medication placed into the canister's dispensing compartment. The supplied canister is taken and placed onto a fulfillment station, as described above, and is scanned into the fulfillment systems memory so the fulfillment system's controller knows the location of the canister, the type of medication that it contains, and the amount of medication within the canister.

As mentioned above, any given fulfillment system may have several fulfillment stations coupled by a conveyor system. However, a labeling station may be located at the starting or input end of the coupled fulfillment stations. The fulfillment system controller instructs the labeling system how to label and identify each medicine bottle. Automated equipment may perform the labeling process. The label or bottle includes ID data, such as a bar code or RFID tag, that matches the ID data of the canister, so that the controller can match the target medication in the canister with the labeled bottle. In a step 620 the label is virtually verified.

After the bottle is properly labeled, it is placed on the conveyor belt, and as it proceeds from one fulfillment station to another, the bottle is scanned or read by an optical scanner or RFID reader and is allowed to pass through, if the bottle's ID data does not match the canister's ID data. It proceeds in this manner from one fulfillment station to a subsequent fulfillment station until it arrives at the fulfillment station that contains the canister whose ID data matches that of the bottle.

When the bottle arrives at the correct station, the above-described system opens the canister, and picks and places the medication in the bottle, until the automated robotic arm places the exact number of tablets or capsules into the labeled bottle. The type and amount of tablets or capsules placed in the bottle is virtually verified in a step 630. The method 600 then ends in a step 640.

The automated medication fulfillment process then continues. When the bottle is filled with the prescribed number of the target medication, the bottle then proceeds through any remaining fulfillment stations until it reaches an automated sealing station where it is hermetically sealed and capped. If the filled bottle is part of a fulfillment order for any given patients or customer, the controller instructs the robotic arm to place the filled bottle in a buffer area within the sealing station until the remaining portions of the order come through the sealing station. When they do arrive, the controller instructs the system to place the buffered bottle back onto the conveyor. This is advantageous in that the entire order of multiple medications can be easily kept together.

The above-described apparatuses or methods may be embodied in, provide by or performed by various conventional digital data processors, microprocessors or computing devices, wherein these devices are programmed or store executable programs of sequences of software instructions to perform one or more of the steps of a method. The software instructions of such programs may be encoded in machine-executable form on conventional digital data storage media that is non-transitory, e.g., magnetic or optical disks, random-access memory (RAM), magnetic hard disks, flash memories, and/or read-only memory (ROM), to enable various types of digital data processors or computing devices to perform one, multiple or all of the steps of one or more of the above-described methods. Additionally, an apparatus, such as a verification controller, may be designed to include the necessary circuitry or programming to perform at least some of the steps as disclosed herein. The verification controller can be a verification controller for a virtual quality control system of an automated medication fulfillment system.

Portions of disclosed embodiments may relate to computer storage products with a non-transitory computer-readable medium that have program code thereon for performing various computer-implemented operations that embody a part of an apparatus, system, carry out the steps of a method set forth herein. Non-transitory used herein refers to all computer-readable media except for transitory, propagating signals. Examples of non-transitory computer-readable media include, but are not limited to: magnetic media such as hard disks, floppy disks, and magnetic tape; optical media such as CD-ROM disks; magneto-optical media such as floptical disks; and hardware devices that are specially configured to store and execute program code, such as ROM and RAM devices. Examples of program code include both machine code, such as produced by a compiler, and files containing higher level code that may be executed by the computer using an interpreter.

Those skilled in the art to which this application relates will appreciate that other and further additions, deletions, substitutions and modifications may be made to the described embodiments. The hardware of components described herein, such as the verification controller, may be of conventional design that is coded with unconventional software programming algorithms to perform the functionality as disclosed herein.

What is claimed is:

1. An automated prescription fulfillment system having multiple filling stations for automatically fulfilling prescriptions of different medications using virtual verifications to satisfy required visual verifications by a pharmacist, comprising:
  a first input location having a first camera for collecting visual verification data of a first verification event;
  a processor configured to receive said visual verification data from the first input location, receive identification data for the first verification event, and generate comparison data from said identification data for the first verification event; and
  a computing device configured to receive at least said comparison data and said visual verification data of said first verification event from said processor and provide at least said comparison data and said visual verification data to a first pharmacist, receive a verification status from said first pharmacist for said first verification event, and send said verification status to said processor, wherein said verification status is based on a virtual review of said comparison data and said visual verification data and said processor is configured to determine when dual verification inputs from said first pharmacist are needed for said verification status;

wherein said first verification event is loading a canister with a source medication from a main supply source, wherein the identification data identifies the source medication, and wherein the virtual review satisfies a visual verification requirement that said source medication was placed into the canister;

a second input location, different from said first input location, having a second camera for collecting visual verification data of a second verification event that is different than said first verification event;

wherein said second verification event is automatically fulfilling a prescription by filling at least a first movable container with at least a quantity of said source medication from said canister, wherein the second verification event is virtually verified by a second pharmacist, via said visual verification data of said second verification event, that satisfies a visual verification requirement that the prescription was properly fulfilled, wherein said visual verification requirements of said first event and said second event are requirements of a government entity; and a conveyor belt that conveys said first movable container to said second input location, wherein said first input location is a fulfillment station for supplying said canister with said source medication independent of said prescription and said second input location is one of the multiple filling stations for placing said quantity of said source medication according to said prescription into said first movable container.

2. The system as recited in claim 1, wherein said first pharmacist is said second pharmacist.

3. The system as recited in claim 1 wherein said identification data is obtained by at least one event monitor at the first input location of said first verification event, wherein said event monitor includes an optical scanner and the identification data includes a label associated with a medicine container of the main supply source.

4. The system as recited in claim 1 wherein said comparison data is a picture.

5. The system as recited in claim 1 wherein said computing device includes a display that simultaneously provides said comparison data and said visual verification data on a display screen for said visual verification of said first verification event by said first pharmacist.

6. A virtual verification system for use by pharmacists with an automated medication fulfillment system, comprising:

cameras, including a first camera configured to obtain first visual verification data of a first event at a first location and a second camera configured to obtain second visual verification data of a second event at a second location, wherein said first event is loading a source medication from a main supply source into a canister and said second event is fulfilling a prescription by loading a quantity of said source medication, according to said prescription, from the canister into a movable container using said automated medication fulfillment system;

an event monitor configured to obtain identification data at said first event, wherein the identification data identifies the source medication being placed into said canister and thereafter the source medication placed into said movable container;

one or more processors configured to receive said first and second visual verification data, receive said identification data, and generate comparison data from said identification data; and one or more computing devices configured to receive said first and second visual verification data and said comparison data from said one or more processors, provide at least said comparison data and said first and second visual verification data to at least one pharmacist, and receive a first verification status and a second verification status from said at least one pharmacist, wherein said first and second verification statuses are based on virtual reviews of one or more of said first visual verification data, said second visual verification data, and said comparison data that satisfy a visual verification requirement by a government entity for said first event and said second event, and wherein at least one of said first verification status or said second verification status is based on two different types of inputs from said at least one pharmacist and said one or more processors determines when said two different types of inputs are required.

7. The system as recited in claim 6 wherein said one or more computing devices include a display and a user interface, wherein said display is configured to simultaneously display said comparison data and said visual verification data for said virtual reviews.

8. The system as recited in claim 6 wherein said first and second visual verification data includes at least an image of the source medication.

9. The system as recited in claim 6 wherein said first event is independent of said prescription.

10. The system as recited in claim 6 wherein said first location includes said second camera and a third camera, wherein said second camera is positioned to look inside said movable container during said fulfilling and said third camera is positioned to capture said source medication going into said movable container during said fulfilling.

11. The system as recited in claim 10 wherein said second visual verification data includes visual images from said second camera and said third camera.

12. The system as recited in claim 6, wherein at least one of the first camera or the second camera can be remotely controlled by said at least one pharmacist to at least zoom in or zoom out.

13. The system as recited in claim 11, wherein one of said second camera and said third camera is a video camera and said other one of said second camera and said third camera is a high speed still camera.

* * * * *